United States Patent
Okamoto

(10) Patent No.: US 9,239,306 B2
(45) Date of Patent: Jan. 19, 2016

(54) ABNORMALITY DIAGNOSIS APPARATUS FOR ELECTRIC PUMP

(71) Applicant: Hitachi Automotive Systems, Ltd., Hitachinaka-shi, Ibaraki (JP)

(72) Inventor: Naoki Okamoto, Isesaki (JP)

(73) Assignee: Hitachi Automotive Systems, Ltd., Hitachinaka-shi (JP)

( * ) Notice: Subject to any disclaimer, the term of this patent is extended or adjusted under 35 U.S.C. 154(b) by 399 days.

(21) Appl. No.: 13/787,927

(22) Filed: Mar. 7, 2013

(65) Prior Publication Data
US 2013/0238147 A1 Sep. 12, 2013

(30) Foreign Application Priority Data
Mar. 8, 2012 (JP) ................. 2012-051411

(51) Int. Cl.
G01N 27/00 (2006.01)
F04D 15/00 (2006.01)
F04D 15/02 (2006.01)
H02H 7/093 (2006.01)
F04B 51/00 (2006.01)
H02P 29/02 (2006.01)

(52) U.S. Cl.
CPC ............... *G01N 27/00* (2013.01); *F04B 51/00* (2013.01); *F04D 15/0088* (2013.01); *F04D 15/0281* (2013.01); *H02H 7/093* (2013.01); *H02P 29/021* (2013.01); *F04B 2203/0201* (2013.01); *F04B 2203/0209* (2013.01)

(58) Field of Classification Search
None
See application file for complete search history.

(56) References Cited

U.S. PATENT DOCUMENTS

| | | | | |
|---|---|---|---|---|
| 6,054,827 A | * | 4/2000 | Takatsuka et al. | 318/474 |
| 2005/0056480 A1 | * | 3/2005 | Sugiyama et al. | 180/421 |
| 2011/0135499 A1 | * | 6/2011 | Lee et al. | 417/44.1 |
| 2011/0264321 A1 | * | 10/2011 | Offerle et al. | 701/29 |
| 2012/0062164 A1 | * | 3/2012 | Sano et al. | 318/721 |

FOREIGN PATENT DOCUMENTS

JP 2006-25493 A 1/2006

* cited by examiner

*Primary Examiner* — Sean Shechtman
(74) *Attorney, Agent, or Firm* — Crowell & Moring LLP

(57) ABSTRACT

An abnormality diagnosis apparatus for an electric pump prevents an erroneous decision that a normally functioning electric pump has an abnormality. When a motor is driven by a current of the driving motor using an upper limit current Iα before a predetermined time T1 passes, it is decided that there is a probability that an abnormality occurs in the pump and the decision is reported to an external device when the number of rotations of the motor is less than the lower limit number of rotations set under lower limit temperature of a hydraulic oil. When the motor is driven by limiting the current of the motor by Iβ and Iγ (<Iα) after T1 passes, it is decided that there is a probability of occurrence of an abnormality when rotation of the motor stops and the decision is reported to the external device.

13 Claims, 7 Drawing Sheets

ABNORMALITY DIAGNOSIS APPARATUS FOR ELECTRIC PUMP

BACKGROUND OF THE INVENTION

1. Field of the Invention

The present invention relates to an abnormality diagnosis apparatus and to a method for an electric pump which supplies a working fluid to, for example, a driving system of a vehicle.

2. Description of the Related Art

With regard to this type of an electric pump, in a technique disclosed in, for example, Japanese Laid-open (Kokai) Patent Application Publication No. 2006-25493, protection control for limiting a current value with respect to a pump driving motor is performed based on a component temperature and a continuous operation time so as to prevent an abnormality caused by heat generation.

According to the disclosure of Japanese Laid-open (Kokai) Patent Application Publication No. 2006-25493, the electric pump is controlled such that an actual number of rotations tracks a commanded value of the number of rotations (the target number of rotations) of the pump driving motor given from an external device irrespectively of a state of the pump side. Therefore, in some cases, the actual number of rotations cannot track the commanded value by way of the protection control.

However, conventionally, according to abnormality diagnosis of the electric pump of this type, it is decided whether or not an abnormality occurs based on tracking (deviation) of the actual number of rotations with respect to the commanded value, and therefore, even if the electric pump is functioning normally, there is a probability that erroneous decision that an abnormality occurs is made.

Furthermore, when an extremely high commanded value is given due to, for example, an abnormality to generate a commanded value or a communication abnormality between the external device and the electric pump (motor driving circuit), the actual number of motor rotations cannot track the commanded value, and thus, in the same way as the above, even if the electric pump is functioning normally, there is a probability that an erroneous decision that an abnormality occurs will be made.

SUMMARY OF THE INVENTION

The present invention is made focusing on such conventional problems, and an object of the present invention is to provide an abnormality diagnosis apparatus for an electric pump capable of preventing an erroneous decision that an abnormality occurs from being made on a normally-functioning electric pump, by performing diagnosis processing taking into account factors which influence abnormality diagnosis.

To achieve the above object, the abnormality diagnosis apparatus for the electric pump according to the present invention is an abnormality diagnosis apparatus for an electric pump which supplies a working fluid based on a command from an external device, and which includes:

a rotation count detecting unit which detects a number of rotations of a motor which drives the electric pump;

a first abnormality deciding preliminary unit which decides that there is a probability of occurrence of an abnormality in the electric pump when detecting a state in which the motor is driven by a current equal to or greater than an upper limit current used during a normal operation and the number of rotations of the motor is less than a lower limit number of rotations which is set based on a working fluid temperature condition; and a second abnormality deciding preliminary unit which decides that there is the probability of occurrence of the abnormality when detecting a state in which the motor is driven with a current limited by a current limit value less than the upper limit current and the number of rotations of the motor is less than a predetermined number of rotations which is set lower than the lower limit number of rotations according to limitation of the current limit value, in which the first abnormality deciding preliminary unit or the second abnormality deciding preliminary unit stops driving of the motor when it is decided that there is the probability of occurrence of the abnormality in the electric pump.

Furthermore, an abnormality diagnosis method for an electric pump according to the present invention is an abnormality diagnosis method of an electric pump which supplies a working fluid based on a command from an external device, and includes the steps of:

detecting a number of rotations of a motor which drives the electric pump;

deciding that there is a probability of occurrence of an abnormality in the electric pump in a first case of having decided a state in which the motor is driven by a current equal to or greater than an upper limit current used during a normal operation and the number of rotations of the motor is less than a lower limit number of rotations which is set based on a working fluid temperature condition;

deciding that there is the probability of occurrence of the abnormality in a second case of deciding a state in which the motor is driven by a current limited by a current limit value less than the upper limit current and the number of rotations of the motor is less than a predetermined number of rotations set lower than the lower limit number of rotations according to limitation of the current limit value; and stopping the motor, in the first case or the second case, when it is decided that there is the probability of occurrence of the abnormality in the electric pump.

Other objects and features of an aspect of the present invention will be understood from the following description with reference to the accompanying drawing.

DESCRIPTION OF THE PREFERRED EMBODIMENTS

Embodiments in which the present invention is applied to an electric pump which supplies hydraulic oil (working fluid) for lubricating and cooling to a continuously variable transmission of a vehicle will be described below.

Figure 1:
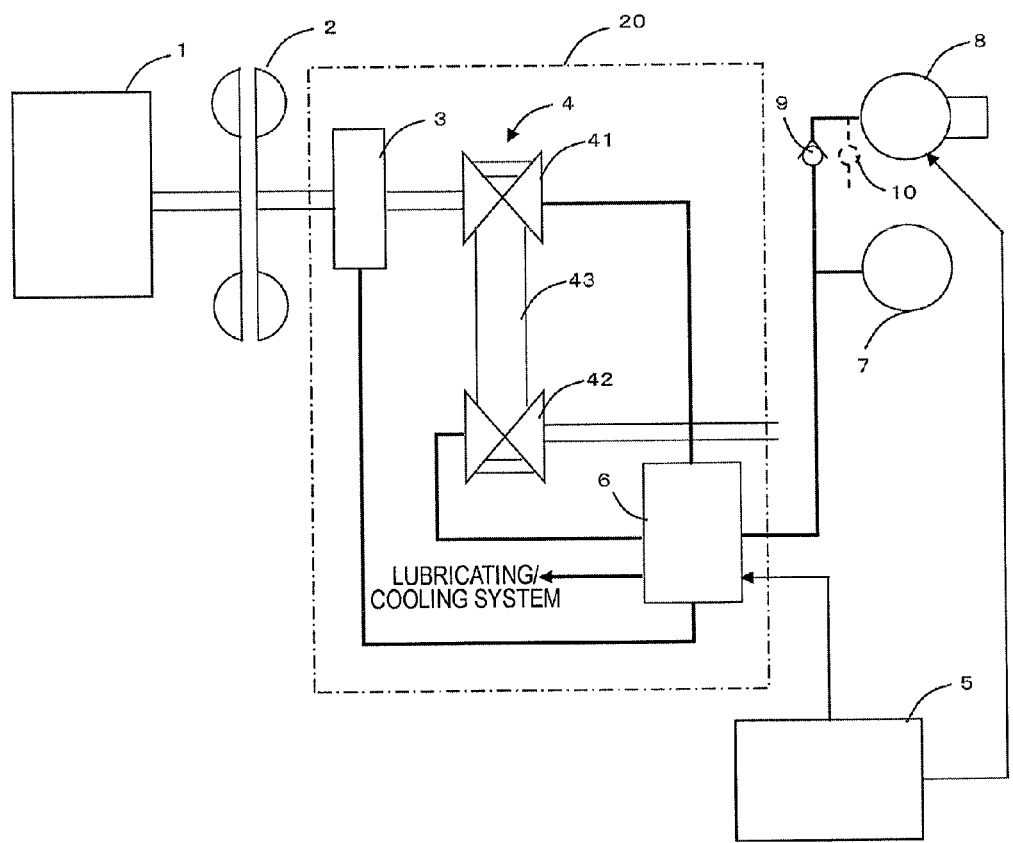
FIG. 1 is a view illustrating a driving force transmission system of a vehicle which has an electric pump according to an embodiment of the present invention.

In FIG. 1, an engine (internal combustion engine) 1 is connected with a continuously variable transmission 4 via a torque converter 2 and a backward and forward switching mechanism 3 which is a start clutch mechanism.

Backward and forward switching mechanism 3 switches between forward movement and backward movement of the vehicle, and includes, for example: a planetary gear train which is formed with a ring gear, a pinion and a pinion carrier jointed to an engine output shaft and a sun gear jointed to a transmission input shaft; a backward brake which fixes a transmission case to the pinion carrier; and a forward clutch which couples the transmission input shaft and the pinion carrier. These backward brake and forward clutch are switched by switching fastening by means of a hydraulic pressure using hydraulic oil shared by continuously variable transmission 4.

Continuously variable transmission 4 has a primary pulley 41, a secondary pulley 42 and a V belt 43 stretched between these pulleys. Rotation of primary pulley 41 is transmitted to secondary pulley 42 through V belt 43, and rotation of secondary pulley 42 is transmitted to driving wheels to drive the vehicle to run.

While the driving force is transmitted, a movable conical plate of primary pulley 41 and a movable conical plate of secondary pulley 42 are moved in a shaft direction to change the radius of position contacting with V belt 43, so that it is possible to change a transmission gear ratio between primary pulley 41 and secondary pulley 42, that is, a rotation ratio.

A transmission mechanism 20 which has these backward and forward switching mechanism 3 and continuously variable transmission 4 is controlled as follows.

A CVT control unit 5 which is an external device computes a transmission control signal based on various signals of the vehicle. A pressure adjusting mechanism 6 which receives the transmission control signal adjusts a discharge pressure from a mechanical pump 7 driven by the engine per each part of transmission mechanism 20, and supplies the pressure to each part.

Meanwhile, an electric pump 8 is disposed in a passage bypassing mechanical pump 7. Electric pump 8 is driven based on a control signal from CVT control unit (CVTCU) 5, serving as the external device, to relax a fastening shock upon restarting after idling stop of the vehicle or to lubricate or cool each lubricated part.

In addition, if necessary, a check value 9 which prevents a reverse flow of hydraulic oil during a normal operation may be disposed in an oil passage at an exit of electric pump 8. Furthermore, as indicated by single dotted chain line in FIG. 1, a relief valve 10 which is opened at the predetermined pressure or less may be provided so as to limit a discharge pressure from electric pump 8 to a predetermined pressure or less.

Figure 2:
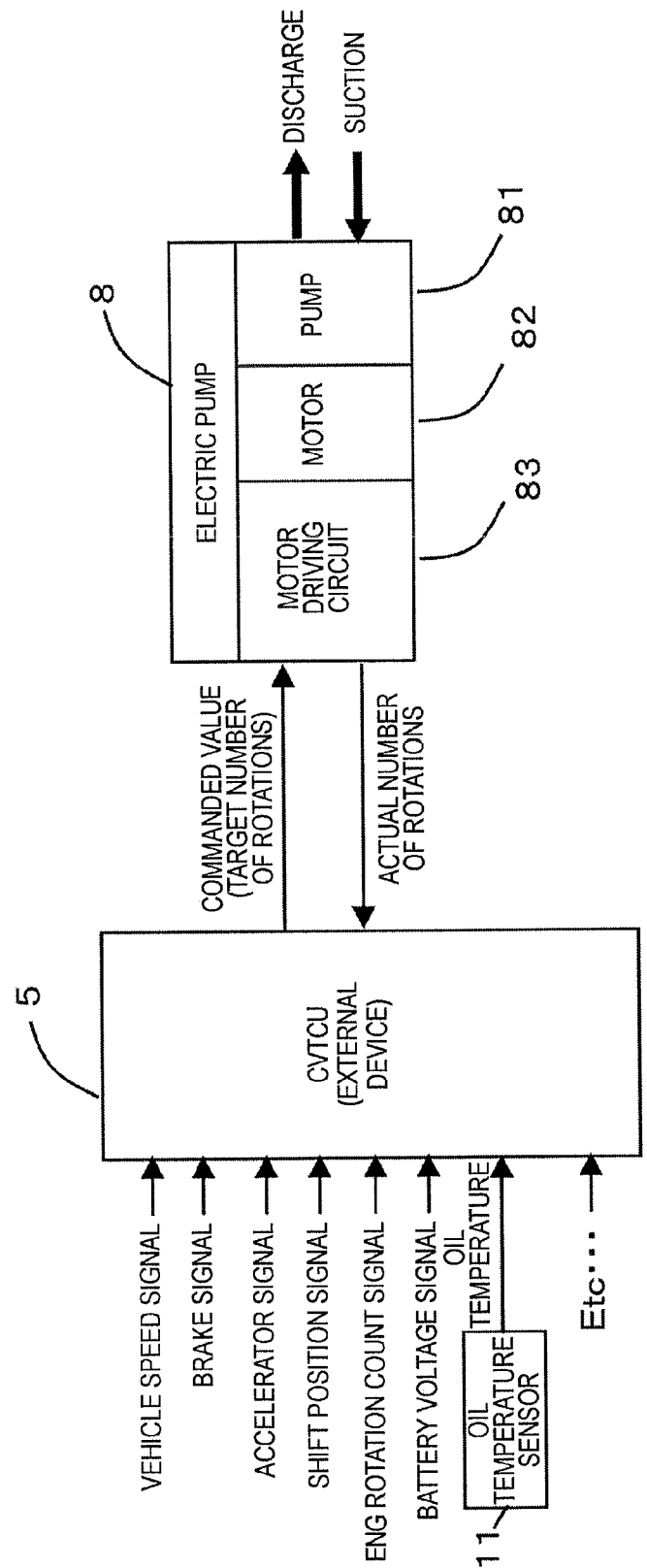
FIG. 2 is a control block diagram of the electric pump.

FIG. 2 is a control block diagram of the electric pump.

CVTCU 5 receives detection signals (vehicle speed, brake, accelerator, shift position, engine rotation speed, battery voltage, and other signals) from various sensors of the vehicle, and a temperature of the hydraulic oil (oil temperature) measured by an oil temperature sensor 11, computes a target number of rotations of electric pump 8 according to a vehicle driving state detected based on these signals, and outputs the target number of rotations to electric pump 8 as a commanded value.

Electric pump 8 has a pump body 81, a motor 82 which drives pump body 81, and a motor driving circuit 83 which drives motor 82.

Motor driving circuit 83 drives motor 82 so that the actual number of rotations are converged to the target number of rotations based on the commanded value from CVTCU 5 while detecting the number of motor rotations (the number of pump rotations) and transmitting the number of motor rotations to CVTCU 5.

Figure 3:
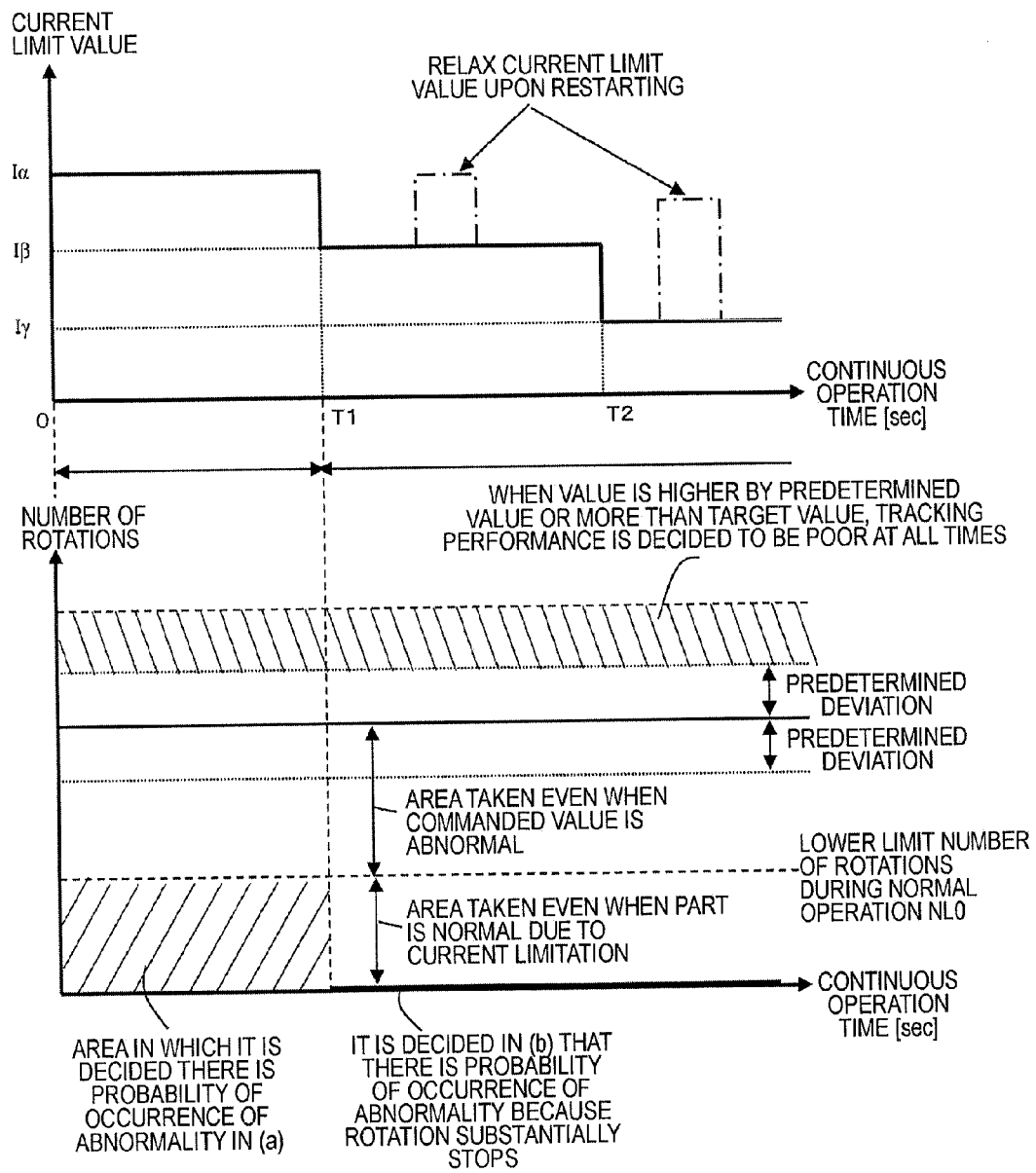
FIG. 3 is a time chart illustrating how the electric pump performs abnormality diagnosis processing.

Here, to prevent occurrence of an abnormality and a decrease in durability due to heat generation of electric pump 8 as illustrated in FIG. 3, a current limit value of motor 82 is set to decrease stepwise according to an increase in a continuous operation time (or a part temperature) after starting.

Meanwhile, in the electric pump 8, by performing processing taking into account current limitation of the motor and abnormality in the commanded value (due to, for example, abnormality to generate the commanded value or communication abnormality between electric pump 8 and CVTCU 5), whether or not there is a probability of occurrence of an abnormality is determined. That is, electric pump 8 (motor driving circuit 83) has a preliminary function of deciding whether or not an abnormality occurs.

Furthermore, when it is decided that there is a probability of occurrence of an abnormality in electric pump 8 (and when abnormality is determined), a signal indicating this decision (instead of an actual rotation count signal) is transmitted to CVTCU 5, and driving of motor 82 is stopped to forcibly stop electric pump 8.

When receiving a signal indicating that there is a probability of occurrence of an abnormality in electric pump 8 from the electric pump 8, CVTCU 5 has a function of deciding whether or not the abnormality of electric pump 8 occurs based on, for example, the oil temperature detected by oil temperature sensor 11 and determining the decision (abnormality decision) that the abnormality occurs. Furthermore, CVTCU 5 performs processing of, for example, maintaining electric pump 8 to be stopped when determining abnormality decision of electric pump 8, and restarting driving after a predetermined time passes when abnormality decision is not determined.

Furthermore, as described below, the electric pump 8 also has a function of determining an abnormality decision according to predetermined processing.

Hereinafter, details of each embodiment of the abnormality diagnosis processing will be described according to a time chart illustrated in FIG. 3 and flowcharts in FIGS. 4 to 8.

Figure 4:
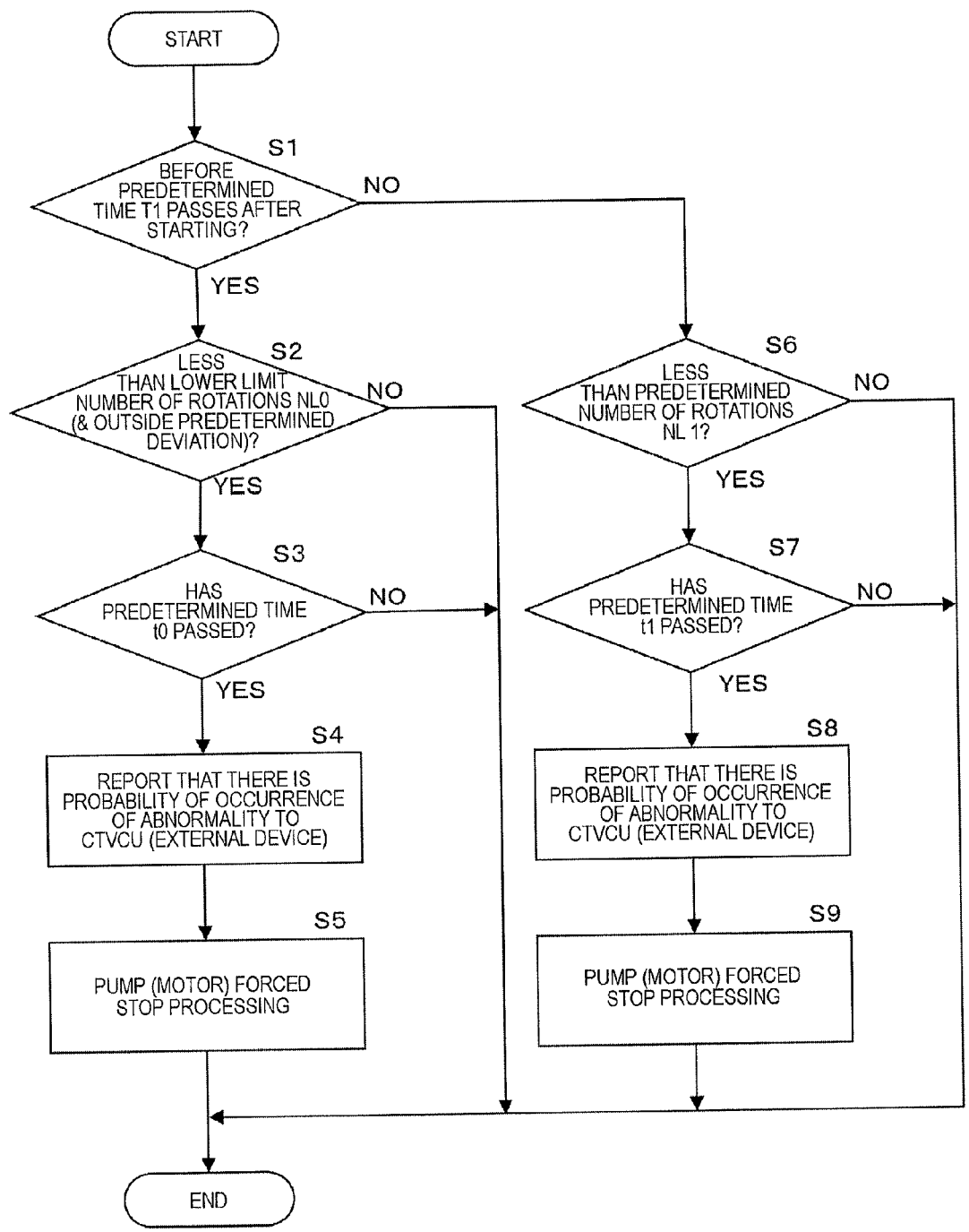
FIG. 4 is a flowchart of the abnormality diagnosis processing according to a first embodiment.

FIG. 4 illustrates an embodiment (first embodiment) of basic processing. This processing is performed in an electric pump 8 (motor driving circuit 83).

In step S1, after electric pump 8 is started, whether or not a predetermined time T1, in which a motor 82 is driven using an upper limit current Iα as a current limit value during a normal operation, has not passed. Here, the upper limit current Iα is set as an upper limit value of the current which is necessary to secure a necessary pump discharge amount under operating temperature conditions.

Before the predetermined time T1 passes, that is, when it is decided that an operation is on-going using the upper limit current Iα as the current limit value, the process proceeds to step S2 to decide whether or not the actual number of rotations of motor 82 (the number of motor rotations=the number of pump rotations) is lower by predetermined deviation or more than the commanded value (the target number of rotations) of the number of motor rotations, and is less than a lower limit number of rotations NL0. The lower limit number of rotations NL0 means, herein, a lower limit number of rotations in an oil temperature range (for example, from −25° C. to 100° C.) which secures an operation of electric pump 8. In general, at a low temperature, leakage amount is small, friction increases, and the number of rotations decreases.

Therefore, the number of rotations at a lower limit temperature (for example, −25° C.) is set as the lower limit number of rotations.

The commanded value set in the CVTCU 5 may, alternatively, be fixed based on a one-to-one relationship with the oil temperature and, in this case, it is also possible to estimate the oil temperature based on the commanded value received in the electric pump 8 and set the lower limit number of rotations based on the estimated oil temperature.

Furthermore, in order to increase precision to decide a probability of occurrence of an abnormality, the conditions to decide that there is a probability of occurrence of an abnormality include that the number of motor rotations is lower by a predetermined deviation or more than the commanded value. When, for example, a commanded value close to the lower limit number of rotations NL0 is generated based on the oil temperature learnt by CVTCU 5 at an extremely low temperature, it is considered that the normal operation is performed even if the number of motor rotations is less than the lower limit number of rotations NL 0, as long as the number of motor rotations is within a predetermined deviation from the commanded value. Therefore, it is possible to avoid a decision that there is a probability of occurrence of an abnormality. However, CVTCU 5 determines a final abnormality decision, and therefore, the decision condition based on the deviation may be omitted from conditions of deciding probability of occurrence of the abnormality in the electric pump 8, for simplicity.

In step S2, when the number of motor rotations is decided to be the lower limit number of rotations NL0 or more, it is decided that an operation is normally performed and the operation is continued as is.

When the number of motor rotations is decided to be less than the lower limit number of rotations NL0 (and outside the predetermined deviation), the process proceeds to step S3 to decide whether or not a predetermined time t0 for deciding the probability of occurrence of an abnormality has passed in this state.

When the number of motor rotations recovers to the lower limit number of rotations NL0 or more in the predetermined time t0, the operation is continued as is.

When the predetermined time t0 passes while the number of motor rotations is less than the lower limit number of rotations NL0 (and outside the predetermined deviation), it is decided that a normal operation is not performed and there is a probability of occurrence of an abnormality in electric pump 8, and the decision that there is the probability of occurrence of an abnormality is reported to CVTCU (external device) 5 in step S4.

Next, in step S5, processing of forcibly stopping driving of electric pump 8 (motor 82) is performed. In this case, the electric pump 8 (motor driving circuit 83) may stop driving, and CVTCU 5 may stop driving the electric pump 8 by transmitting a signal (driving amount 0) to stop driving electric pump 8 to electric pump 8 in response to the received decision that there is the probability of occurrence of an abnormality.

When it is decided that the predetermined time T1 has passed after the starting of electric pump 8 in step S1, that is, after an operation is switched to an operation using a current limit value (Iβ or Iγ) lower than the upper limit current Iα during the normal operation, the process proceeds to step S6.

In step S6, it is decided whether or not the number of motor rotations has decreased to a predetermined number of rotations NL1 or less in the case in which electric pump 8 is operated with a limited current. In this step, the predetermined number of rotations NL1 is set to a value close to a value when the motor stops, and it is decided that motor 82 (pump) actually stops when the number of motor rotations is the predetermined number of rotations NL1 or less. This is because, due to limitation of a current in addition to abnormality in a commanded value (generation abnormality or communication abnormality), even if no abnormality occurs in electric pump 8, there is a possibility that the number of motor rotations decreases to the number of motor rotations in a state in which the motor is stopped or is close to being stopped.

When the number of motor rotations decreases to the predetermined number of rotations NL1 or less and it is decided that the motor is in a substantially stopped state, the process proceeds to step S7 to decide whether or not the predetermined time t1 has passed in this state. When the number of motor rotations reaches the predetermined number of rotations NL1 or more in the predetermined time t1 and motor rotation recovers, the operation is continued as is.

When it is decided in step S7 that the number of motor rotations is the predetermined number of rotations NL1 or less, that is, the predetermined time t1 has passed while the motor stops, the process proceeds to step S8.

Similar to steps S4 and S5, in steps S8 and S9, a decision that the normal operation is not performed and there is a probability of occurrence of an abnormality of electric pump 8 is reported to CVTCU (external device) 5, and driving of electric pump 8 (motor 82) is forcibly stopped.

In the processing according to the first embodiment, under operating conditions using the upper limit current Iα as the current limit value before the predetermined time T1 passes, a necessary pump discharge amount under the operating conditions is secured even if a commanded value becomes excessively high, tracking the commanded value of the actual number of rotations is delayed, and the actual number of rotations decreases by a predetermined deviation or more, as long as the number of motor rotations is the lower limit number of rotations NL0 or more. Consequently, driving of electric pump 8 is continued as is.

Thus, by deciding the probability of occurrence of an abnormality using the lower limit number of rotations NL0 which is set taking into account working fluid conditions (lower limit temperature) while the pump is used, it is possible to prevent an erroneous decision, in conventional manner, that an abnormality of electric pump 8 occurs based on a relationship (deviation) between a commanded value and the actual number of rotations, and to prevent electric pump 8 from being stopped due to the erroneous decision, and electric pump 8 may contribute to enhancement of the operability (a rise in a hydraulic pressure) of CVT (operating device) as much as possible.

When the actual number of rotations is less than the lower limit number of rotations NL0, the necessary pump discharge amount under the above-described operating conditions is not secured and there is a probability of occurrence of an abnormality of electric pump 8. However, the number of rotations less than the lower limit number of rotations NL0 is not caused by an abnormality but by, for example, an extremely low temperature in which the number of rotations hardly rises. Consequently, without determining an abnormality decision, it is possible to report a decision that there is a probability of occurrence of an abnormality to CVTCU (external device 5), and leave a final abnormality decision to CVTCU (external device) 5 having oil temperature information.

That is, in a case in which there is no abnormality in electric pump 8, it is also possible to prevent an erroneous decision resulting from determination of the decision that an abnormality occurs in electric pump 8.

Furthermore, under the operating conditions in which a current limit value after the predetermined time T1 passes is limited to Iβ or Iγ, even if electric pump 8 is normal, the number of rotations may decrease to the number of rotations in a state in which the motor is stopped or is close to being stopped due to not only a decrease in the number of rotations caused by abnormality in a commanded value but also limitation of a motor current.

Hence, when the number of rotations of electric pump 8 reaches the predetermined number of rotations NL1 or more in the predetermined time T1 and rotation is detected, it is possible to contribute to enhancement of the operability of a CVT hydraulic pressure as much as possible by continuing the operation of electric pump 8 as is.

Meanwhile, when it is decided that electric pump 8 is in a stopped state after the predetermined time T1 passes, it is possible to report a decision that there is a probability of occurrence of an abnormality to CVTCU (external device) 5, and leave a final abnormality decision to CVTCU (external device) 5.

Thus, after the predetermined time T1 passes, the probability of occurrence of an abnormality is decided based on the predetermined number of rotations NL1 which is set taking into account limitation of a motor current, in addition to a decrease in the number of rotations due to abnormality in a commanded value and a communication abnormality. Therefore, it is possible to prevent an erroneous decision that an abnormality of electric pump 8 occurs, based only on a deviation between the commanded value and the actual number of rotations. Furthermore, it is possible to prevent electric pump 8 from stopping due to the erroneous decision, and contribute to an increase of a CVT (operating device) hydraulic pressure by electric pump 8 as much as possible.

Furthermore, although, either before or after the predetermined time T1 passes, when it is decided that there is a probability of occurrence of an abnormality, there is a possibility that the durability of the electric pump is affected by driving of the motor (pump). However, it is possible to avoid the influence on the durability of the electric pump by stopping the driving.

Figure 5:
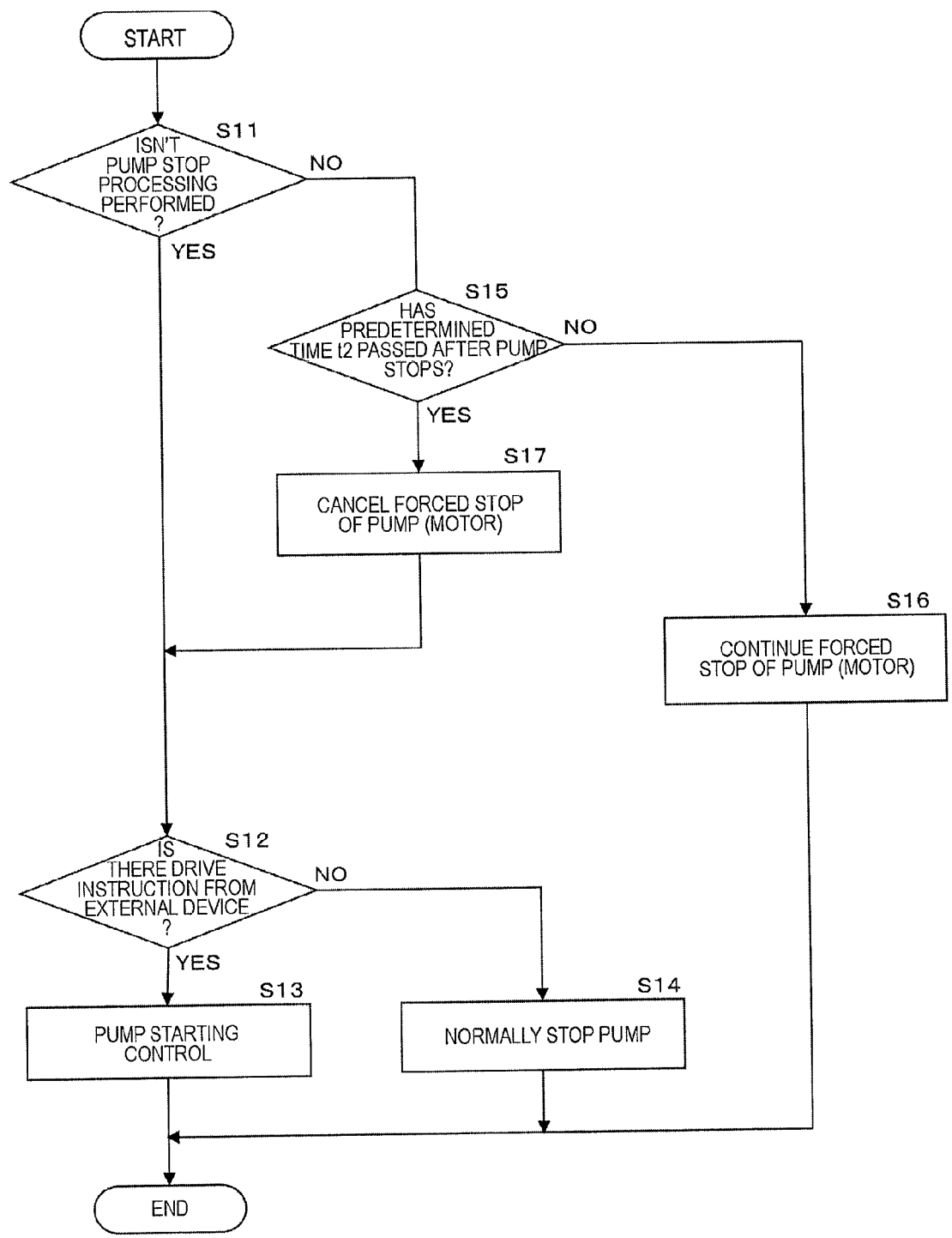
FIG. 5 is a flowchart of abnormality diagnosis processing according to a second embodiment.

FIG. 5 illustrates an embodiment (second embodiment) of processing performed in an electric pump 8 after processing according to the first embodiment.

In step S11, it is decided whether or not driving stop processing is performed following a decision that there is a probability of occurrence of an abnormality in electric pump 8.

When it is decided that stop processing is not performed and electric pump 8 is normally operated, the process proceeds to step S12 to decide whether or not there is a drive instruction from CVTCU (external device) 5.

When there is the drive instruction, starting of the electric pump (motor 82) is controlled based on a commanded value (the target number of rotations) in step S13. When there is not a drive instruction, normal stop processing of electric pump 8 is performed in step S14 to stop electric pump 8.

When it is decided in step S11 that drive stop processing of electric pump 8 (motor 82) is performed, the process proceeds to step S15 to decide whether or not a predetermined time t2 has passed after driving of the pump is stopped. Before the predetermined time t2 passes, drive stop processing is continued in step S16, and after the predetermined time t2 passes, the process proceeds to step S17 to cancel the drive stop processing. Here, the predetermined time t2 is set to a time which is necessary for the oil temperature to rise by a predetermined temperature, and the predetermined temperature is set to, for example, a value corresponding to the amount of variation of an oil temperature sensor 11. That is, although the commanded value is usually set based on the oil temperature detected by oil temperature sensor 11, taking into account that an oil temperature detected by the oil temperature sensor varies in a range in which the detected oil temperature is higher than an actual oil temperature, a rise in the oil temperature corresponding to the amount of variation is obtained as the predetermined time passes.

That is, even if the target number of rotations is set higher due to the above variation of the oil temperature sensor in the high temperature range, the actual oil temperature is low, hydraulic oil viscosity is significant, and rotation of electric pump 8 hardly rises. Therefore, it may be decided that there is a probability of occurrence of an abnormality. Furthermore, a rise in the number of rotations may be prevented as a motor current increases and the current is limited due to current limitation. In the above cases, as the predetermined time t2 passes, the oil temperature rises, viscosity of the hydraulic oil decreases, and the hydraulic oil is more easily discharged, so that there is a possibility that the number of motor rotations (the number of pump rotations) rises to the target number of rotations.

Hence, the process proceeds to step S12 and subsequent steps to perform control of starting electric pump 8 or normal stop processing according to a drive instruction from CVTCU (external device) 5.

According to the configuration of the second embodiment, after electric pump 8 is forcibly stopped, forced stop is canceled after a predetermined time passes. Accordingly, when the number of rotations rises to the number of rotations corresponding to a normal operation such that it is not decided that there is a probability of occurrence of an abnormality due to a rise in the oil temperature as the time passes, the operation is continued as is. That is, it is possible to relax limitation in starting of CVT (operating device) so as to contribute to enhancement of the operability while preventing an erroneous decision of an abnormality.

Figure 6:
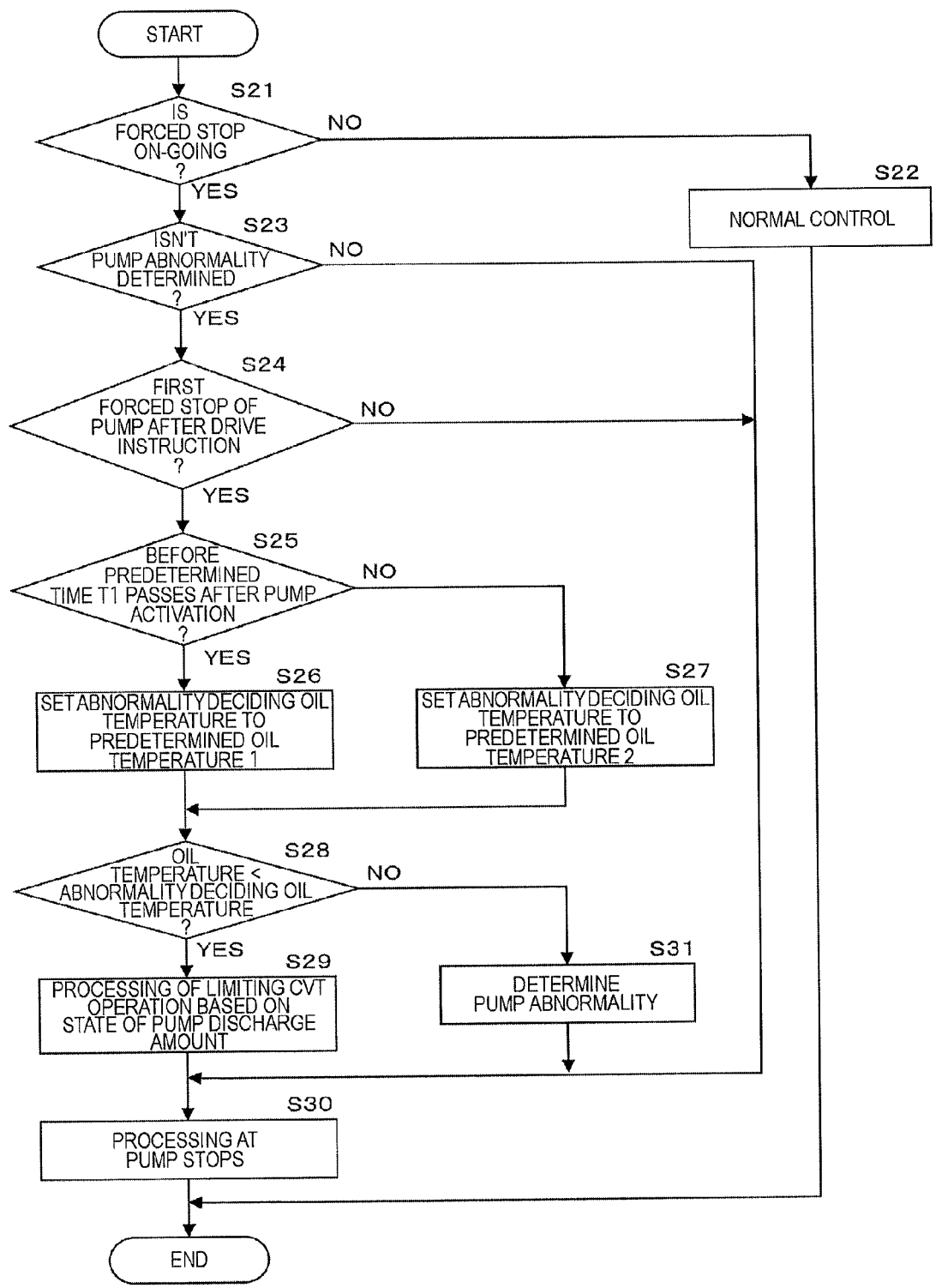
FIG. 6 is a flowchart of abnormality diagnosis processing according to a third embodiment.

FIG. 6 illustrates an embodiment (third embodiment) of abnormality diagnosis processing including abnormality decision determination in a CVTCU 5.

In step S21, whether or not an electric pump 8 is forcibly stopped is decided. When electric pump 8 is not forcibly stopped, normal control of electric pump 8 is continued in step S22. When electric pump 8 is forcibly stopped, the process proceeds to step S23.

In step S23, it is decided whether or not an abnormality of the pump is yet to be determined. When the abnormality is determined, the process proceeds to step S30 to continue processing applied when the pump stops.

When the abnormality is not determined, the process proceeds to step S24 to decide whether or not the pump is forcibly stopped for the first time after the drive instruction. If not, the process proceeds to step S30 to continue processing applied when the pump stops.

When it is decided that the pump is forcibly stopped for the first time, the process proceeds to step S25 to decide whether or not a predetermined time T1 passes after the pump is started.

When it is decided that T1 has yet to pass, that is, an operation is on-going using an upper limit current Iα as a current limit value during a normal operation, an abnormality deciding oil temperature is set to a predetermined temperature 1 in step S26. When it is decided that an operation is on-going using Iβ or Iγ as a current limit value after T1 passes, the abnormality deciding oil temperature is set to a predetermined temperature 2 in step S27.

Here, the predetermined temperature 1 and the predetermined temperature 2 are set as follows. Under respective operating conditions, friction upon driving of a pump due to a decrease in viscosity of the hydraulic oil is maintained at a predetermined value or less at the predetermined temperature 1 and the predetermined temperature 2 or more. The predetermined temperature 1 and the predetermined temperature 2 are set to limit temperatures at which the number of pump rotations reaches or exceeds predetermined numbers of rotations NL0 and NL1, at which it is not decided that there is a probability of occurrence of an abnormality, as long as electric pump 8 is normally functioning. Note that the predetermined temperature 1 and the predetermined temperature 2 are set to the temperature to which the amount of variation of oil temperature sensor 11 in the high temperature range is added.

Next, in step S28, whether or not the oil temperature is less than the abnormality deciding oil temperatures (the predetermined temperature 1 and the predetermined temperature 2) is decided. When the oil temperature is less than the abnormality deciding oil temperatures, it may be decided in step S4 or step S8 in FIG. 4 that there is a probability of occurrence of an abnormality due to a low oil temperature, and therefore, the process proceeds to step S29 without determining an abnormality decision.

In step S29, when it is decided that there is a probability of occurrence of an abnormality, as illustrated in FIG. 5, even if forced stop of electric pump 8 is subsequently canceled to restart electric pump 8 after a predetermined time passes, there is a probability that the necessary discharge amount cannot be acquired because the number of rotations of electric pump 8 is sufficient or electric pump 8 stops. Therefore, processing of limiting an operation of CVT which is an operating device (for example, setting a lower adjusting oil pressure) is performed.

In step S30, processing applied when the pump stops is continued.

When the oil temperature is decided to be the abnormality deciding oil temperatures (the predetermined temperature 1 and the predetermined temperature 2) or greater, it is decided that abnormality occurs irrespectively of the oil temperature, that is, some sort of abnormality such as an abnormality in a component of electric pump 8 occurs, diagnosis that an abnormality has occurred is determined in step S31, and the processing applied when the pump stops is continued in step S30.

According to a configuration of the third embodiment, it is possible to precisely determine an abnormality decision based on a fact that the pump rotation is not normal despite a rise in the oil temperature to the abnormality deciding oil temperatures (the predetermined temperature 1 and the predetermined oil temperature 2) or greater.

Figure 7:
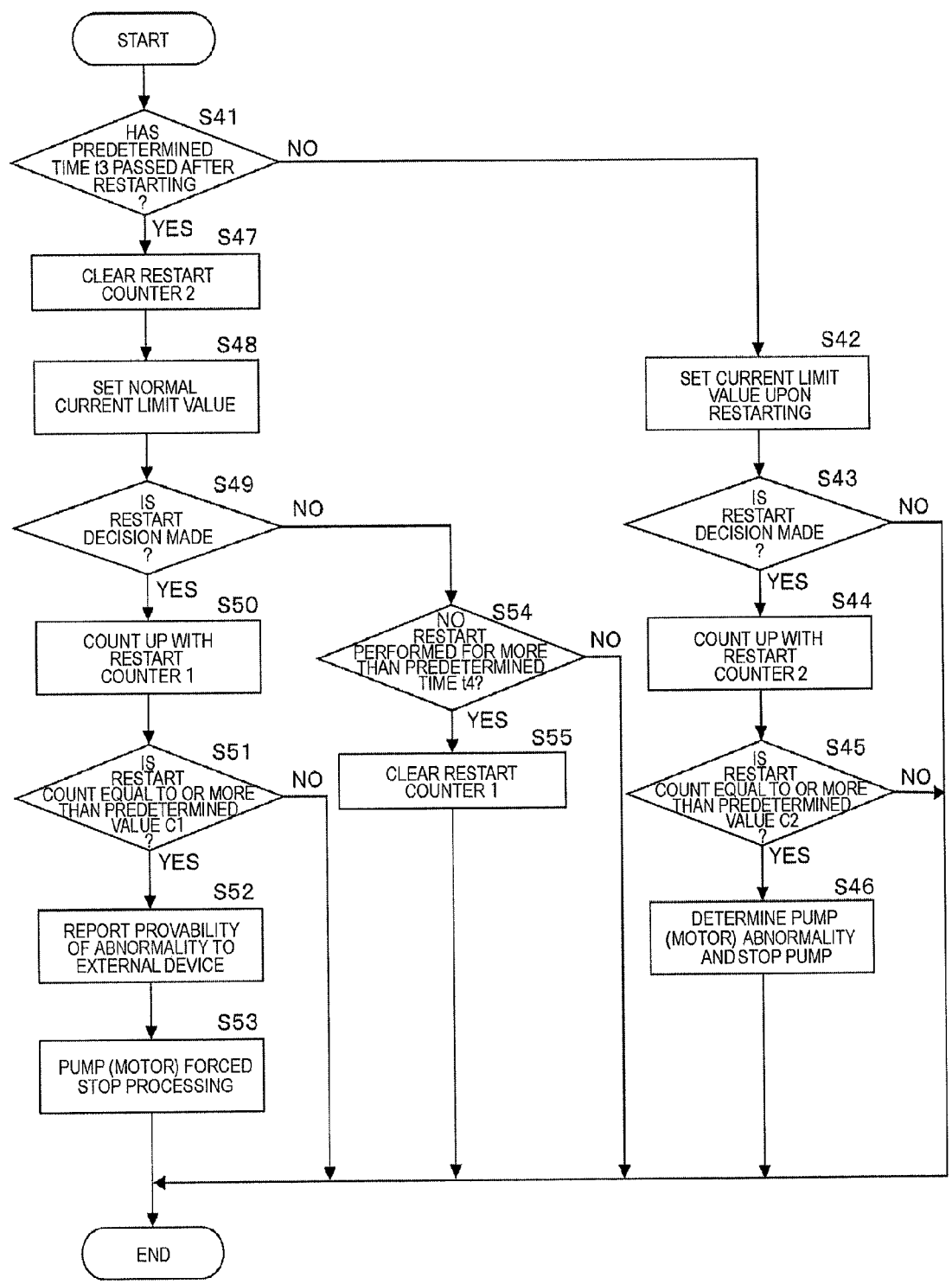
FIG. 7 is a flowchart of abnormality diagnosis processing according to a fourth embodiment.

FIG. 7 illustrates an embodiment (fourth embodiment) of abnormality diagnosis processing including abnormality decision determination in an electric pump 8.

In the present embodiment, when electric pump 8 stops while electric pump 8 is driven in a state in which a motor current is limited after a predetermined time T1 passes, limitation of the motor current is relaxed, and control of restarting electric pump 8 is immediately performed.

Electric pump 8 is stopped in the abovementioned state due to, for example, abnormality in a commanded value (generation abnormality or communication abnormality), limitation of an excessive current which is not suitable to an actual oil temperature, or occurrence of an abnormality in electric pump 8.

In step S41, after electric pump 8 is restarted in the abovementioned state, whether or not a predetermined time t3 has passed is decided.

Immediately after the restarting, it is decided that the predetermined time t3 has not passed, and the process proceeds to step S42 to set a current limit value Ix corrected for the restart. As indicated by single dotted chain line in FIG. 3, the current limit value Ix increases to a value which is greater than a normal current limit value $\beta$ or $\gamma$ set depending on a time passed after electric pump 8 is restarted, and which is an upper limit current $\alpha$ or less. By increasing the current limit value and performing the restart processing, a rise in the number of rotations is facilitated.

Next, in step S43, while the operation is on-going using the corrected current limit value, whether or not restart is decided again, that is, whether or not it is decided that electric pump 8 is in a stopped state. Hence, when electric pump 8 does not rotate even after the restarting, another decision on whether to restart is made.

Furthermore, when a restart decision is made, the process proceeds to step S44 to count up a restart counter 2 used during an operation in which the current limit value is increased.

Next, in step S45, whether or not a restart decision count counted by restart counter 2 reaches a predetermined count C2 or more. When it is decided that the restart decision count reaches the predetermined count C2 or greater, the process proceeds to step S46 to determine that an abnormality occurs in electric pump 8 (a motor and a driving circuit) and stop the driving.

Thus, when the number of pump rotations does not rise even during an operation with an increased current limit value (in a substantially stopped state), an abnormality is determined without deciding an abnormality based on the oil temperature. Even if a decrease in the number of rotations due to abnormality in a commanded value (generation abnormality or communication abnormality) is taken into account, the motor is configured to be allowed to rotate due to the increase in the current limit value Ix as long as the electric pump 8 is normally functioning, so that it is possible to determine that abnormality occurs in electric pump 8 even when the stopped state is continued.

After the restarting in step S41, when it is decided that electric pump 8 rotates and the predetermined time t3 has passed while no abnormality is determined, the process proceeds to step S47 to clear a count value of restart counter 2.

Next, in step S48, a current limit value is set back to a current limit value which does not include an increase of the current limit value indicated above and is appropriate for a time passed after normal restarting.

Similar to step S43, in step S49, it is decided whether or not restart is decided when electric pump 8 does not rotate.

When the restart is decided, the process proceeds to step S50 to count up a restart counter 1 for normal current limitation.

In step S51, whether or not the restart decision count reaches the predetermined count C1 or greater is decided. When it is decided that the restart decision count reaches the predetermined count C1 or greater, the process proceeds to step S52.

In step S52, it is reported that there is a probability of occurrence of an abnormality in electric pump 8 to CVTCU (external device) 5.

In step S53, driving of electric pump 8 (motor) is stopped.

Thus, when a current is limited by a normal current limit value appropriate for a time passed after restarting, there is a probability that electric pump 8 stops. Therefore, it is reported that there is the probability of occurrence of an abnormality without determining an abnormality decision, and the CVTCU (external device) 5 decides whether or not that an abnormality occurs based on the oil temperature.

According to the fourth embodiment, by relaxing the current limit value upon restarting, in the electric pump 8, it is possible to determine an abnormality decision according to whether or not electric pump 8 rotates.

Note that, although not described in the above embodiments, when the number of pump rotations is higher, by a predetermined deviation or greater, than a commanded value (the target number of rotations) as illustrated in FIG. 3, the CVTCU 5 only needs to decide that tracking performance is poor.

Although the present invention is applied to a control apparatus for an electronic pump which generates a transmission hydraulic pressure in the above embodiments, the present invention is applicable to, for example, a running motor of a hybrid vehicle or a control device of an electric pump used to, for example, cool an inverter likewise, and the same effect can be obtained.

The entire contents of Japanese Patent Application No. 2012-51411, filed Mar. 8, 2012, are incorporated herein by reference.

While only a select embodiment has been chosen to illustrate the present invention, it will be apparent to those skilled in the art from this disclosure that various change and modification can be made herein without departing from the scope of the invention as defined in the appended claims.

Furthermore, the foregoing description of the embodiments according to the present invention is provided for illustration only, and not for the purpose of limiting the invention, the invention as claimed in the appended claims and their equivalents.

What is claimed is:

1. An abnormality diagnosis apparatus for an electric pump which supplies a working fluid based on a command from an external device, the abnormality diagnosis apparatus comprising:
   a rotation count detecting unit that detects a number of rotations of a motor which drives the electric pump; and
   a processing unit which decides in a first series of steps that there is a probability of occurrence of an abnormality in the electric pump when detecting a state in which the motor is driven by a current equal to or greater than an upper limit current used upon a normal operation and the number of rotations of the motor is less than a lower limit number of rotations which is set based on a working fluid temperature condition, and which decides in a second series of steps that there is the probability of occurrence of the abnormality when detecting a state in which the motor is driven with a current limited by a current limit value less than the upper limit current and the number of rotations of the motor is less than a predetermined number of rotations which is set lower than the lower limit number of rotations according to limitation of the current limit value indicating that the motor is stopped or close to being stopped,
   wherein the motor is stopped by the external device when it is decided that there is the probability of occurrence of the abnormality in the electric pump.

2. The abnormality diagnosis apparatus for the electric pump according to claim 1, wherein, when a predetermined time passes after the motor is stopped based on the decision that there is the probability of occurrence of the abnormality in the electric pump, driving of the motor is resumed based on a drive instruction from the external device.

3. The abnormality diagnosis apparatus for the electric pump according to claim 1, wherein, in a case in which the processing unit, in the first series of steps or the second series of steps, decides that there is the probability of occurrence of the abnormality in the electric pump, the processing unit determines that the abnormality occurs in the electric pump when it is decided that a temperature of the working fluid is equal to or greater than a first temperature or a second temperature used to decide an abnormality.

4. The abnormality diagnosis apparatus for the electric pump according to claim 1, wherein, in a case in which the processing unit, in the first or the second series of steps, decides that there is the probability of occurrence of the abnormality in the electric pump, the stopped motor is restarted and an operation of a working fluid using device is limited in response to a discharge state of the electric pump upon the restarting when it is decided that a temperature of the working fluid is equal to or greater than a first temperature and a second temperature used to decide an abnormality.

5. The abnormality diagnosis apparatus for the electric pump according to claim 1, wherein, when the operation of the electric pump is stopped while the electric pump is driven, the processing unit corrects the current limit value to increase, makes a restart decision for restarting the motor while limiting a current based on the current limit value corrected to increase, and returns the current limit value to an original current limit value when a predetermined time passes after the motor is restarted based on the restart decision.

6. The abnormality diagnosis apparatus for the electric pump according to claim 5, wherein the processing unit determines the decision that the abnormality occurs in the electric pump when the restart decision is made a plurality of number of times before the predetermined time passes.

7. An abnormality diagnosis apparatus for an electric pump which supplies a working fluid based on a command from an external device, the abnormality diagnosis apparatus comprising:
   a rotation count detecting means which detects a number of rotations of a motor which drives the electric pump; and
   a processing means for deciding, in a first series of steps, that there is a probability of occurrence of an abnormality of the electric pump when detecting a state in which the motor is driven by a current equal to or greater than an upper limit current used during a normal operation and the number of rotations of the motor is less than a lower limit number of rotations which is set based on a working fluid temperature condition, and for deciding, in a second series of steps, that there is the probability of occurrence of the abnormality when detecting a state in which the motor is driven by a current limited by a current limit value less than the upper limit current and the number of rotations of the motor is less than a predetermined number of rotations set lower than the lower limit number of rotations according to limitation of the current limit value, indicating that the motor is stopped or close to being stopped,
   wherein the external device stops the motor when it is decided that there is the probability of occurrence of the abnormality in the electric pump.

8. An abnormality diagnosis method for an electric pump which supplies a working fluid based on a command from an external device, the abnormality diagnosis method comprising the steps of:
   detecting a number of rotations of a motor which drives the electric pump;
   deciding that there is a probability of occurrence of an abnormality in the electric pump in a first case of having detected a state in which the motor is driven by a current equal to or greater than an upper limit current used during a normal operation and the number of rotations of the motor is less than a lower limit number of rotations which is set based on a working fluid temperature condition;

deciding that there is the probability of occurrence of the abnormality in a second case of having detected a state in which the motor is driven by a current limited by a current limit value less than the upper limit current and the number of rotations of the motor is less than a predetermined number of rotations set lower than the lower limit number of rotations according to limitation of the current limit value, indicating that the motor is stopped or close to being stopped; and stopping the motor in the first case or the second case when it has been decided that there is the probability of occurrence of the abnormality in the electric pump.

9. The abnormality diagnosis method for the electric pump according to claim 8, wherein, when a predetermined time passes after the motor is stopped based on the decision that there is the probability of occurrence of the abnormality in the electric pump, resuming driving of the motor based on a drive instruction from the external device.

10. The abnormality diagnosis method for the electric pump according to claim 8, further comprising determining that the abnormality occurs in the electric pump when it is decided from a temperature of the working fluid that is equal to or greater than an abnormality deciding first temperature or second temperature, that there is the probability of occurrence of the abnormality in the electric pump.

11. The abnormality diagnosis method for the electric pump according to claim 8, further comprising, in a case in which it is decided that there is the probability of occurrence of the abnormality in the electric pump, when it is decided that a temperature of the working fluid is less than an abnormality deciding first temperature or second temperature, restarting the stopped motor, and limiting an operation of a working fluid using device depending on a discharge state of the electric pump upon the restarting.

12. The abnormality diagnosis method for the electric pump according to claim 8, when an operation is stopped while the electric pump is driven, further comprising correcting the current limit value to increase, making a restart decision for restarting the motor while limiting a current based on the current limit value corrected to increase, and returning the current limit value to an original current limit value when a predetermined time passes after the motor is restarted based on the restart decision.

13. The abnormality diagnosis method for the electric pump according to claim 12, further comprising making a decision that the abnormality occurs in the electric pump when the restart decision is made a plurality of number of times before the predetermined time passes.

* * * * *